(12) United States Patent
Jones

(10) Patent No.: US 10,537,727 B2
(45) Date of Patent: Jan. 21, 2020

(54) STERILE CONNECTION ACCESS SYSTEM FOR FLUID FITTINGS

(71) Applicant: Avasys, LLC, Columbia, MD (US)

(72) Inventor: Cameron C. Jones, Columbia, MD (US)

(73) Assignee: Avasys, LLC, Columbia, MD (US)

(*) Notice: Subject to any disclaimer, the term of this patent is extended or adjusted under 35 U.S.C. 154(b) by 119 days.

(21) Appl. No.: 15/711,034

(22) Filed: Sep. 21, 2017

(65) Prior Publication Data

US 2018/0078753 A1 Mar. 22, 2018

Related U.S. Application Data

(60) Provisional application No. 62/397,413, filed on Sep. 21, 2016.

(51) Int. Cl.
| | | |
|---|---|---|
| *A61M 25/16* | (2006.01) | |
| *A61M 25/18* | (2006.01) | |
| *A61M 39/00* | (2006.01) | |
| *A61M 39/10* | (2006.01) | |
| *A61M 39/18* | (2006.01) | |
| A61M 39/24 | (2006.01) | |
| A61M 39/02 | (2006.01) | |

(52) U.S. Cl.
CPC ............ *A61M 39/18* (2013.01); *A61M 39/10* (2013.01); *A61M 2039/0036* (2013.01); *A61M 2039/0276* (2013.01); *A61M 2039/1083* (2013.01); *A61M 2039/1088* (2013.01); *A61M 2039/2433* (2013.01)

(58) Field of Classification Search
CPC .......... A61M 2039/0036; A61M 39/10; A61M 39/18; A61M 2039/0276; A61M 2039/1083; A61M 2039/1088; A61M 2039/2433; A61M 39/14; A61M 39/045; A61M 39/26; A61M 39/1011
USPC .................................................. 604/533–539
See application file for complete search history.

(56) References Cited

U.S. PATENT DOCUMENTS

| | | | | |
|---|---|---|---|---|
| 4,610,469 A | * | 9/1986 | Wolff-Mooij | A61M 39/045 251/149.1 |
| 2005/0087715 A1 | * | 4/2005 | Doyle | A61M 39/045 251/149.1 |
| 2005/0090805 A1 | * | 4/2005 | Shaw | A61M 39/26 604/523 |

(Continued)

*Primary Examiner* — Rebecca E Eisenberg
(74) *Attorney, Agent, or Firm* — Mintz Levin Cohn Ferris Glovsky and Popeo, P.C.; Peter F. Corless; Carolina E. Säve

(57) ABSTRACT

A fluid connection system and a method of attaching the same are provided to create a sterile fluid-flow path. The connection system includes a fluid access device having a female connector with a female elastomeric member disposed at a proximal end thereof and is coupled to an internal surface of the fluid access device. A male connector is coupled to an external surface of the female elastomeric member. Additionally, a male elastomeric member is disposed within the distal end of the male connector and seals a distal opening thereof. At least one aperture is disposed through a sidewall of the distal end of the male connector. An internal cannula is exposed out of the female connector to open the female elastomeric member upon engagement with the male connector. The male connector is sealed to the female connector by the male elastomeric member.

28 Claims, 12 Drawing Sheets

(56) References Cited

U.S. PATENT DOCUMENTS

| | | | | |
|---|---|---|---|---|
| 2007/0066965 A1* | 3/2007 | Coambs | ............... | A61M 39/26 604/533 |
| 2008/0287920 A1* | 11/2008 | Fangrow | ............ | A61M 39/1011 604/535 |
| 2010/0021230 A1* | 1/2010 | Olivier | ................. | A61M 39/10 403/11 |
| 2015/0297459 A1* | 10/2015 | Sanders | ............... | A61J 1/2096 604/414 |

* cited by examiner

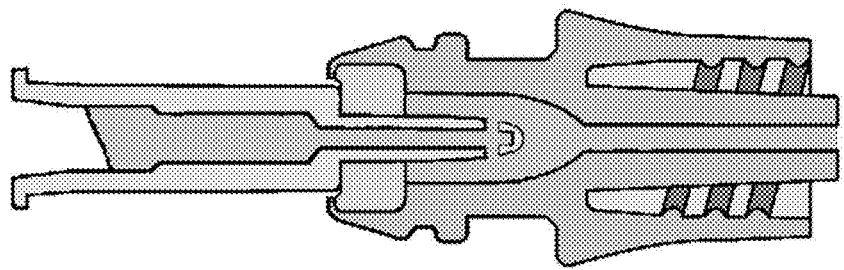
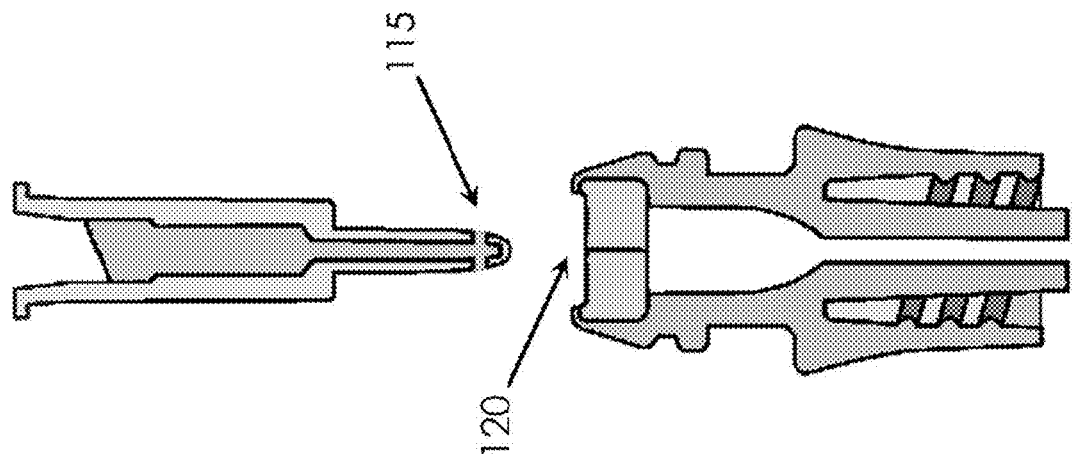
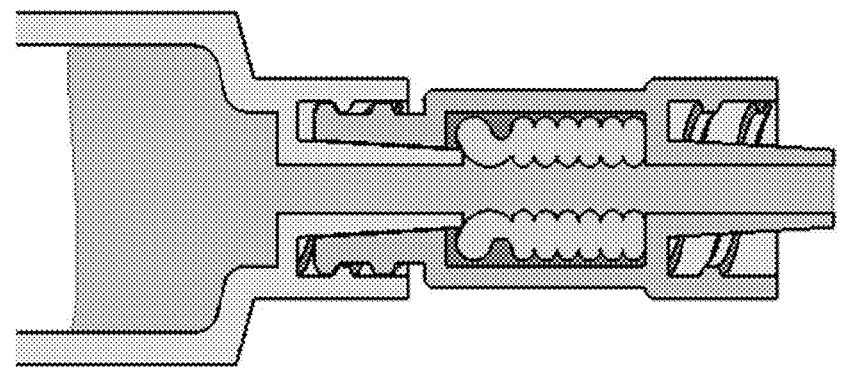
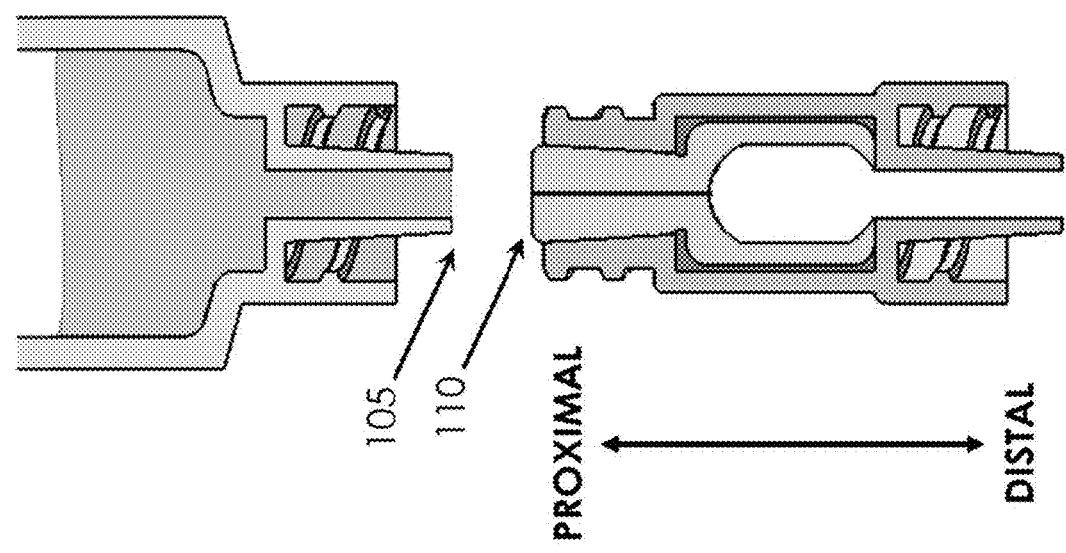

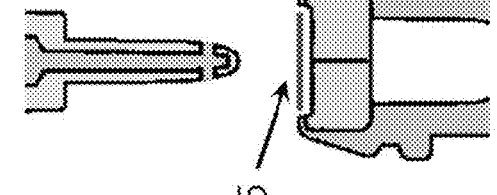
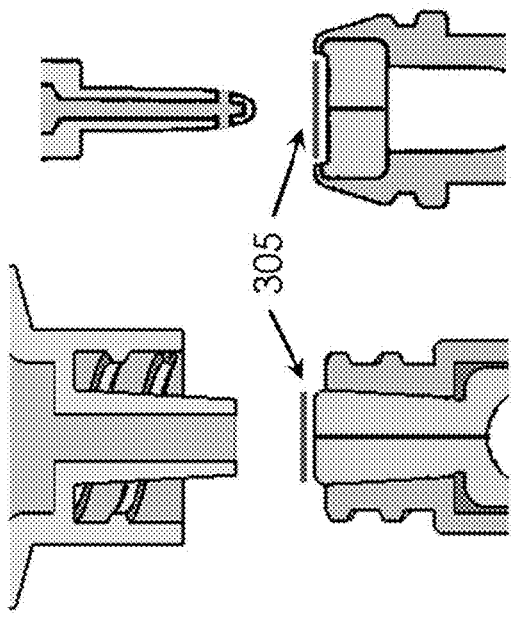
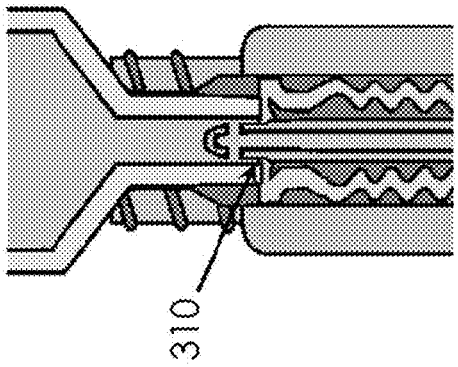
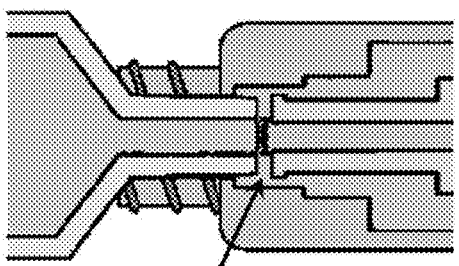
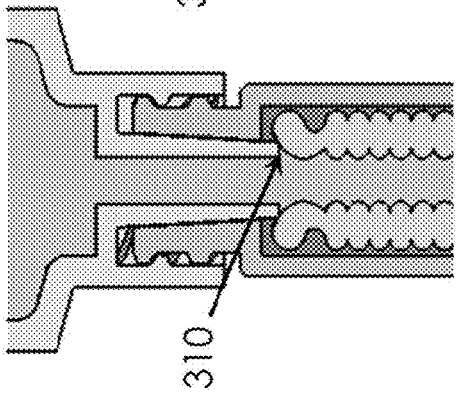

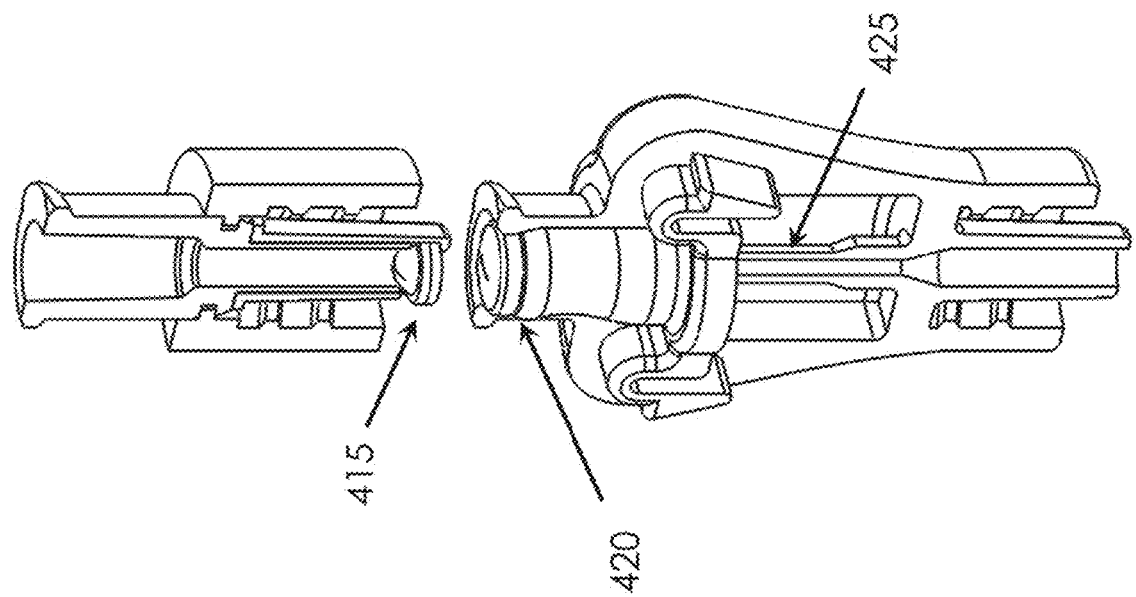
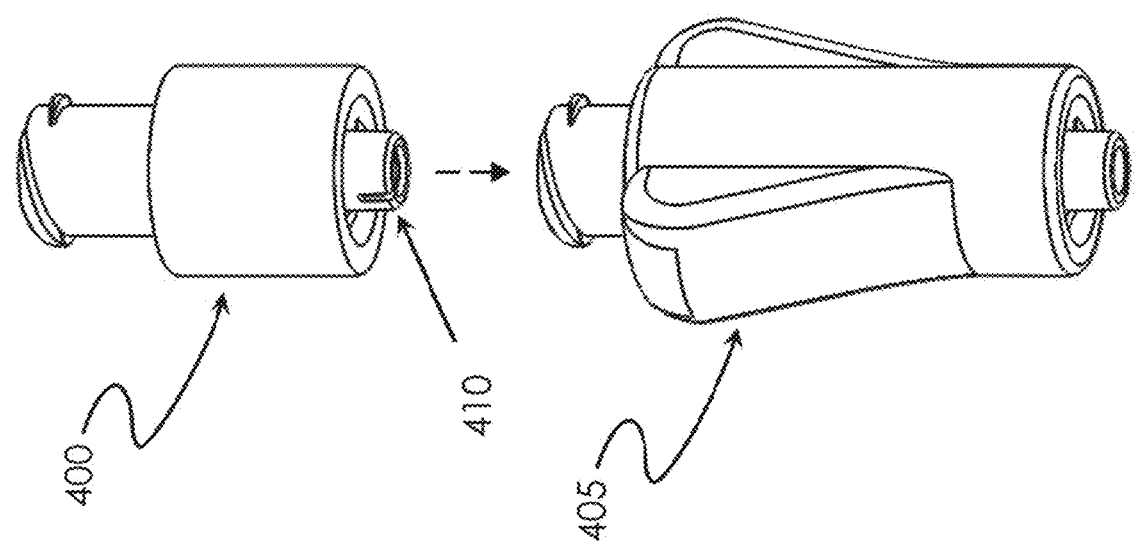

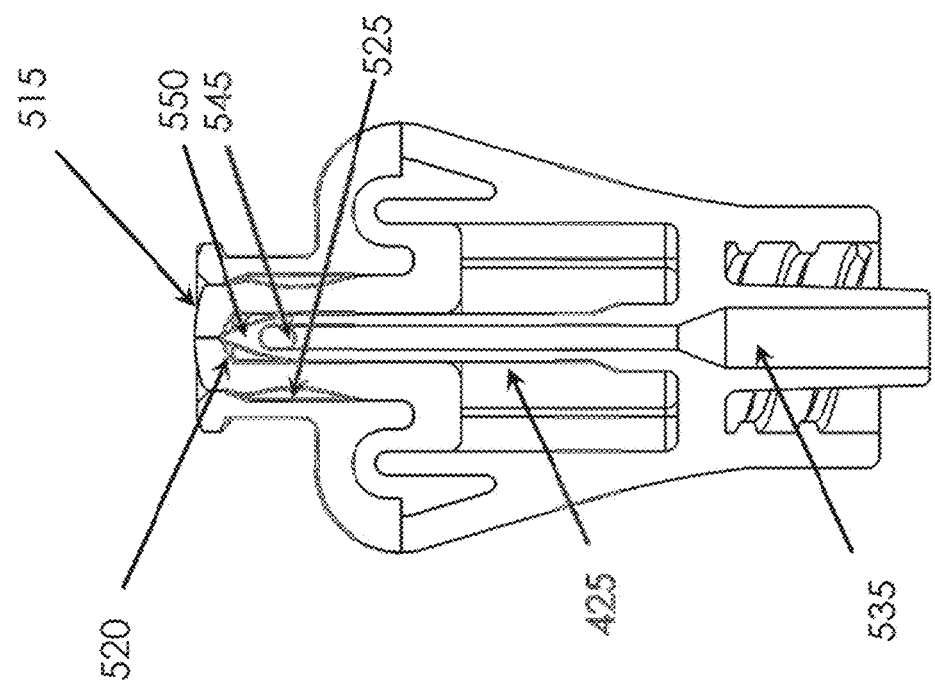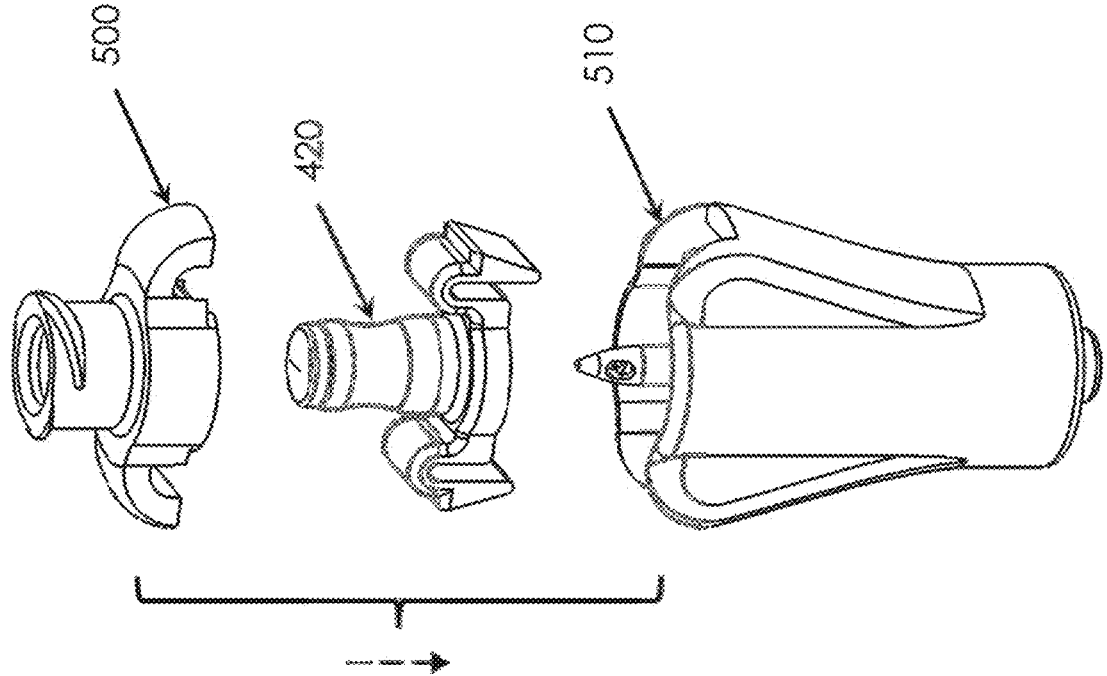

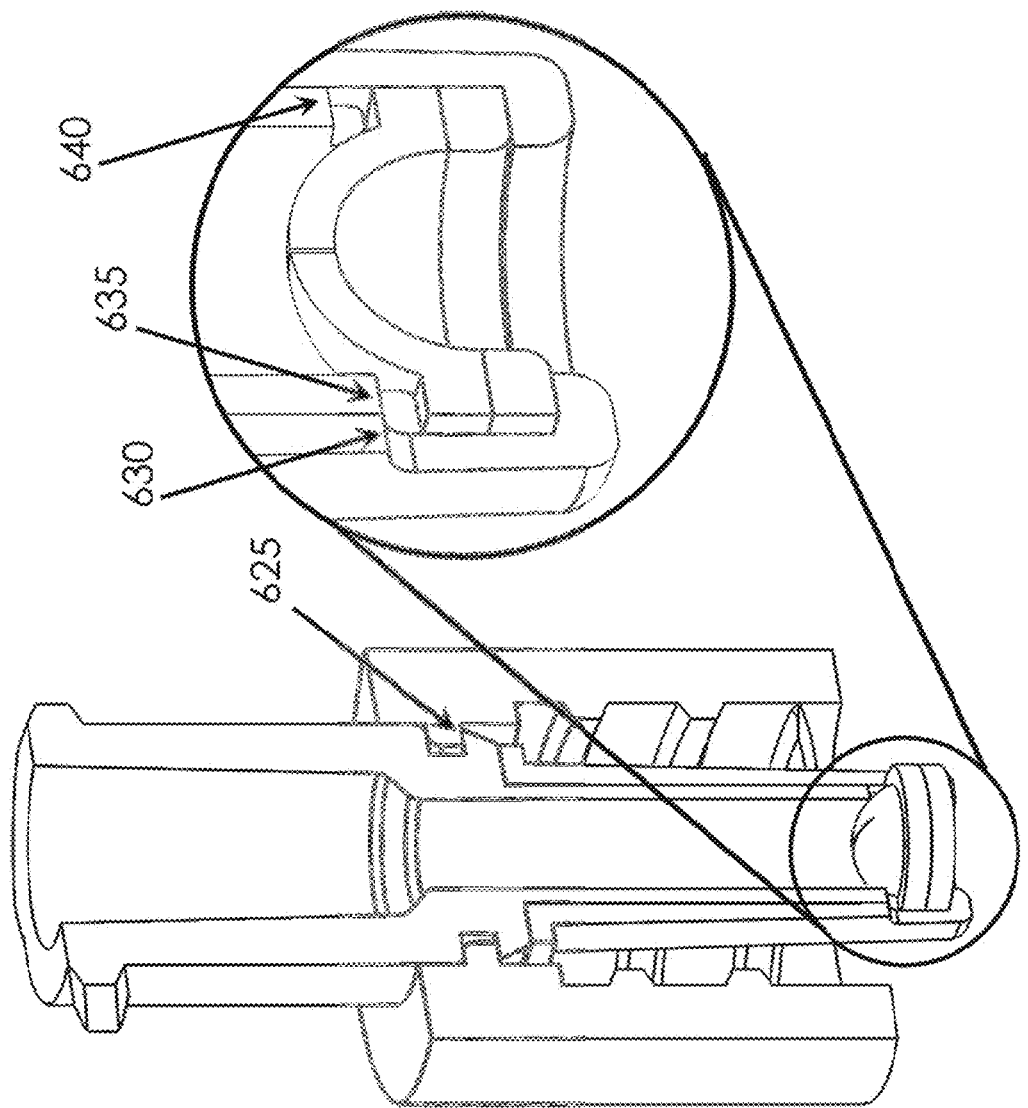

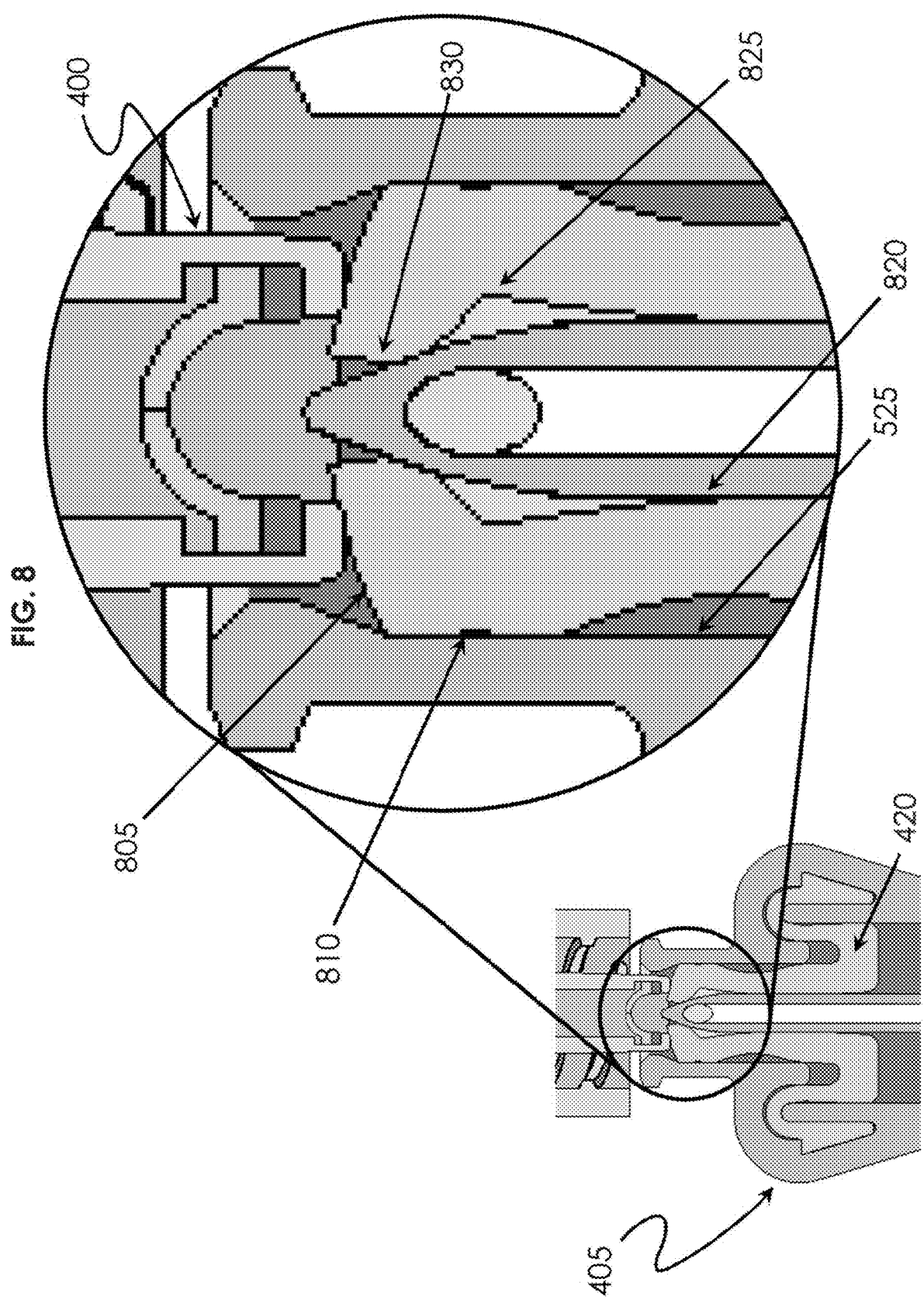

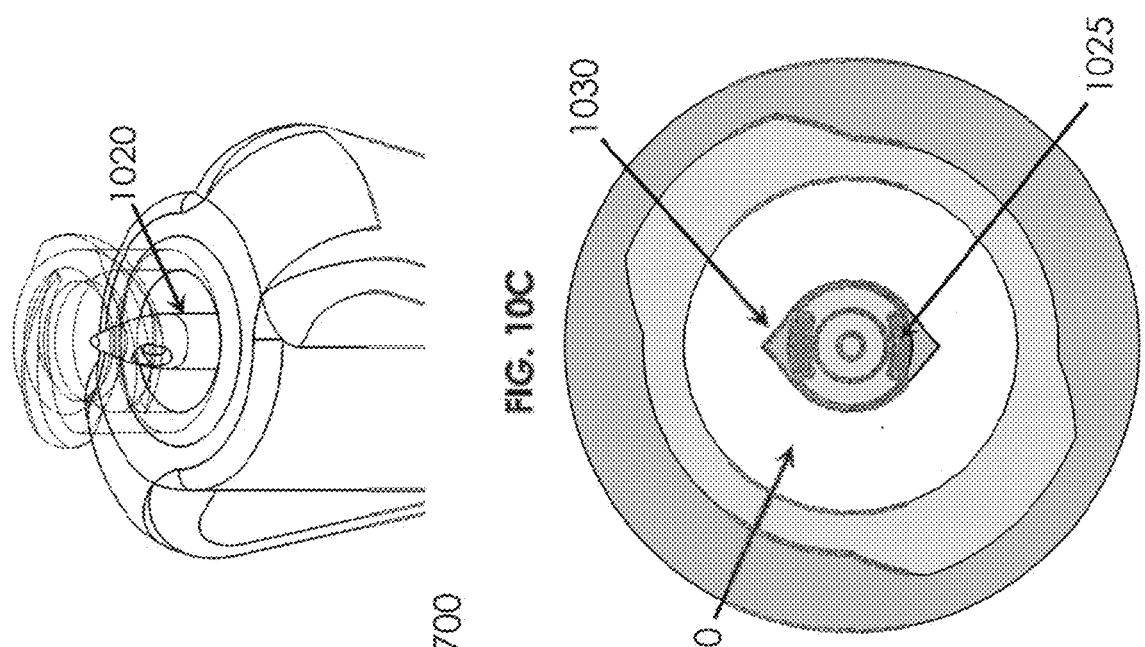
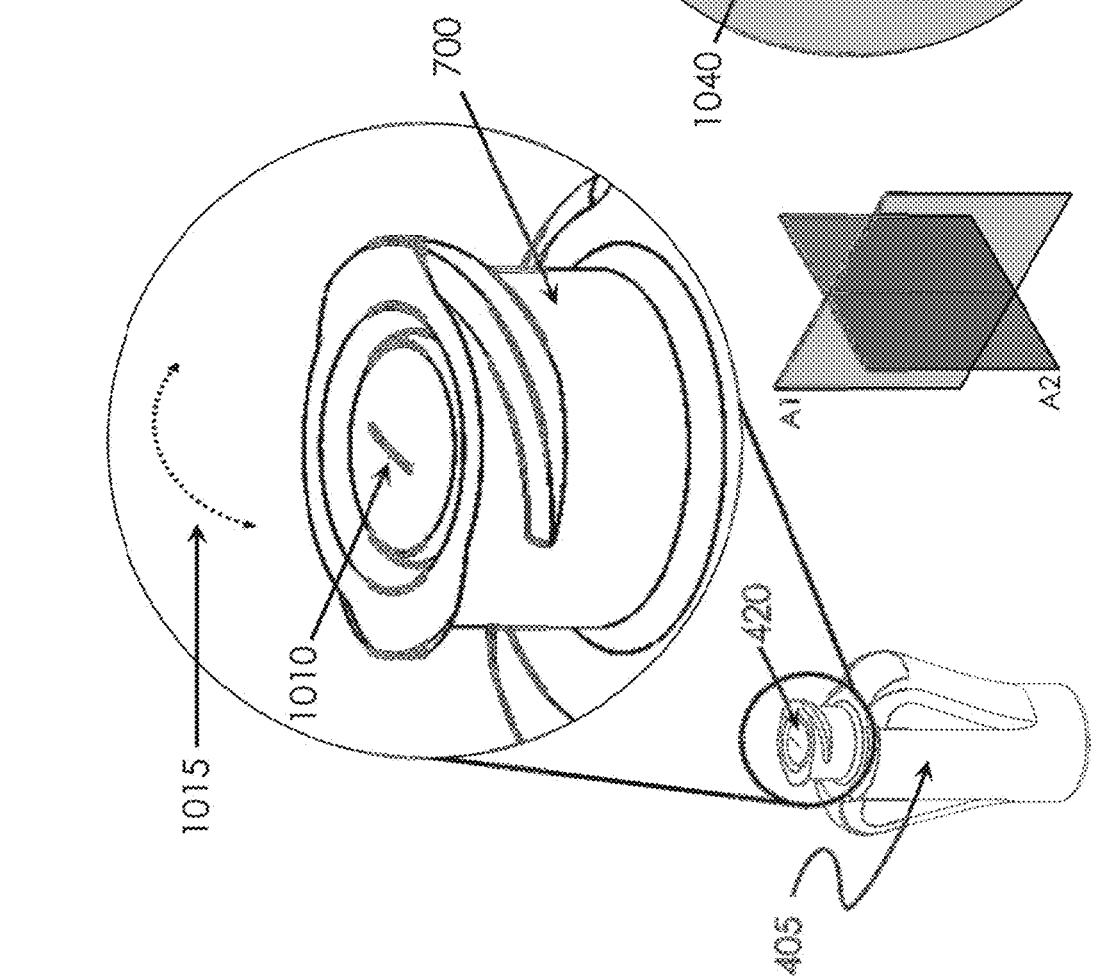

STERILE CONNECTION ACCESS SYSTEM FOR FLUID FITTINGS

FIELD OF INVENTION

The present invention relates to a fluid access system, and more particularly, relates to a sterile connection access system that prevents contaminant ingress during a connection sequence between fluid fittings, such as those commonly used in the medical field.

BACKGROUND

Applications in the medical field requiring aseptic connecting interfaces include bioprocessing, nutrition support, drug delivery, and vascular access procedures among many others. These applications often require coupling at least two fluid connectors in a non-sterile setting in order to transfer a sterile fluid from one sterile site to another.

One common device used in infusion therapy markets are needle-free devices, which may be attached to a variety of ports, vials, or other connectors such as those located at the proximal end of an indwelling vascular catheter.

FIGS. 1A-1D show various types of needle-free devices according to the related art. In particular, FIGS. 1A-1D illustrate the mechanism by which two types of needle-free systems function, demonstrating the attachment of a male needleless connector to the female connector on the proximal end of a needleless adapter, and a re-sealable elastomeric septum disposed within the needleless adapter. The needleless adapter illustrated in FIG. 1A is often called a luer access device (LAD), since it allows an attaching medical article with a male luer tip to create a fluid-tight connection with a distal fluid system. The series FIGS. 1A-1B shows a male luer tip 105 used to depress a re-sealable split septum 110 within the female connector to provide fluid communication. FIGS. 1C and 1D show the male connector as a blunt-tip cannula 115 used to access a re-sealable split septum 120 disposed within the female connector at the proximal end of the needleless device.

FIGS. 2A-2D show various types of needleless fluid systems of the related art. In particular, FIG. 2A shows a needle-free device with a single septum that is displaced upon attachment of the male connector. The device contains no internal features apart from the re-sealable septum. FIG. 2B shows a type of needle-free device that includes an internal actuator to achieve positive fluid displacement upon detachment of the male connector. The positive fluid displacement causes the fluid to flow between the outer housing and the internal actuator component and results in a small release of fluid through the distal tip. FIGS. 2C and 2D show a device containing an internal blunt-tip cannula which pierces a split septum as the elastomeric septum is displaced within the device upon attachment of the male connector. Fluid flows through the blunt tip cannula within the device and through the distal tip. This design results in a neutral fluid displacement as the withdrawal of the male connector causes the septum to re-seat around the internal cannula with minimal fluid displacement (usually less than ±10 microliters).

In non-sterile environments, microbial contamination between fluid fittings such as those used in needle-free systems occurs when the interface between the male and female tips is not adequately disinfected prior to attaching the connecting article. When used in patient care settings, contamination may result in an increased risk of infection as organisms may be spread to other surfaces along the distal fluid lumen as well as to the patient.

Needleless systems that do not isolate the infusion fluid from poorly disinfected external surfaces, such as those in FIGS. 3A and 3B, are more susceptible to device contamination since the sterile fluid contained within the attaching article may potentially contact a surface pathogen 305. Likewise, devices whose external surface(s) touch internal features of the fluid flow channel 310, such as those in FIGS. 3C-3E, are also susceptible to a higher risk of device contamination since microbial transfer can occur between these surfaces in the event of inadequate disinfection. In this latter case, future disinfection procedures that address only external surfaces of the device will be insufficient in preparing the device for access since internal features cannot be disinfected.

As shown by the discussion of the related art above, currently available needle-free systems have design features that can lead to microbial transfer between external sources and aseptic fluid systems. Accordingly, it would be advantageous to provide a needle-free system that is capable of providing an aseptic connection by preventing exposed surfaces on the female connector from contaminating both the attaching male connector and internal surfaces which are part of the fluid flow pathway.

SUMMARY

The present invention provides a fluid access system that achieves a sterile connection between male and female connectors to thus reduce potential transfer of microbial organisms from external sources into a fluid system.

According to one aspect of the present invention, the fluid access system includes a male connector in the form of a male luer connector and an access device in the form of a luer access device (LAD) that includes of a female connector compatible with a male luer fitting, an internal female elastomeric member disposed at a proximal end thereof, and an internal cannula disposed within the device. The female elastomeric member of the access device is furthermore coupled to an internal surface of the device. In addition, the male connector of the fluid access system is coupled to an external surface of the female elastomeric member. At least one elastomeric member is disposed within the male connector tip and seals an opening of a distal end of the male connector. At least one aperture is disposed through a sidewall of the distal end of the male connector. Further, the female elastomeric member may seal an internal cannula disposed within the proximal portion of the access device, and upon engagement with the male connector, the internal cannula may penetrate the female elastomeric member and be exposed within the female connector. An elastomeric member within the male connector tip may also seal an opening of the aperture disposed through a sidewall of the male connector by the penetration of the internal cannula.

In an additional aspect, an elastomeric member in the male connector may seal an opening of the aperture concurrently when the female elastomeric member is opened to provide fluid communication between the male connector and the female connector. Particularly, a portion of the female elastomeric member may move down along the internal cannula upon engagement with the male connector to expose an internal cannula. The female elastomeric member may undergo elastic deformation upon engagement with the male connector, and return to an original position following removal of the male connector.

In another aspect, an interior of the male connector may be threaded to engage with an external wall of the female connector. The distal end of the male connector may also include a plurality of apertures. Alternatively, the plurality of apertures may be formed as slots.

In yet another aspect, the elastomeric member of the male connector tip may include at least two separate elastomeric members. In particular, one elastomeric member may be of an annular shape having an inner diameter approximately equal to the outer diameter of the internal cannula of the access device, and the other elastomeric member may be a valve or split septum which opens in response to a further advancement of the male connector with the internal cannula of the access device.

In one aspect of the present invention, a proximal portion of the female elastomeric member may contain a valve or split septum through which the internal cannula may penetrate, and which may close sufficiently upon returning to an initial position to prevent fluid flow through the internal cannula.

According to another aspect of the present invention, a method is provided for coupling a fluid access system. The method may include sealing a distal end of a male connector using at least one elastomeric member and coupling the male connector to an external surface of a female elastomeric member that is disposed at a proximal end of the access device. An internal cannula disposed in a passageway of the female connector penetrates through the female elastomeric member to open the female elastomeric member. Additionally, an opening of at least one aperture is sealed using the male elastomeric member as the internal cannula penetrates through the female elastomeric member and the male elastomeric member. The aperture is particularly disposed through a sidewall of the distal end of the male connector.

In a further aspect, the female elastomeric member may be coupled to an internal wall of the access device, while the female elastomeric member deforms during the opening thereof to prevent an outer surface from contacting the internal cannula. A portion of the female elastomeric member may include a resilient section that undergoes elastic deformation upon coupling of the female connector and male connector. Upon detachment of the male connector, the resilient section returns a proximal portion of the female elastomeric member to an initial position, which prevents fluid flow in the internal cannula and orients the outer surface of the female elastomeric member external to the fluid access device.

According to yet another aspect of the present invention, a coupling method is provided for a fluid access system that may include coupling a female elastomeric member to an internal wall of the fluid access device and coupling an internal cannula into an end of the female elastomeric member within a passageway of the female connector. A male connector is coupled to the female connector causing the female elastomeric member to be opened by penetration of the internal cannula of the fluid access device. Further, the female elastomeric member deforms during the opening thereof to prevent an outer surface from contacting the internal cannula. When the female elastomeric member is opened, the internal cannula penetrates into the male connector to couple the male connector and the female connector and provide a fluid communication there between.

In yet another aspect of the present invention, the male and female connectors are not tapered connectors. That is, the male and female connectors are not limited to being formed as tapered connectors. Moreover, an elastomeric member of the male connector may provide a fluid-tight seal between the male connector and female connector.

Notably, the present invention is not limited to the combination of the fluid access system elements as listed above and may be assembled in any combination of the elements as described herein.

Other aspects of the invention are disclosed infra.

BRIEF DESCRIPTION OF THE DRAWINGS

The embodiments herein may be better understood by referring to the following descriptions in conjunction with the accompanying drawings in which like reference numerals indicate identically or functionally similar elements, of which:

FIGS. 1A-1D are views of needle-free fluid systems including luer activated devices and blunt-tip cannulas according to the related art;

FIGS. 3A-3E are views of contamination susceptibility of needle-free systems according to the related art;

FIGS. 4A-4B are views of a fluid access system according to an exemplary embodiment of the present invention;

FIGS. 5A-5B are assembly views of a fluid access device according to an exemplary embodiment of the present invention;

FIGS. 6A-6C are assembly and detailed views of a male connector according to an exemplary embodiment of the present invention;

FIG. 8 is a detailed view of a female elastomeric member in an opened state according to an exemplary embodiment of the present invention;

FIGS. 10A-10C are detailed views of the female elastomeric member and opening method by an internal cannula according to an exemplary embodiment of the present invention;

DETAILED DESCRIPTION

Figure 2A:
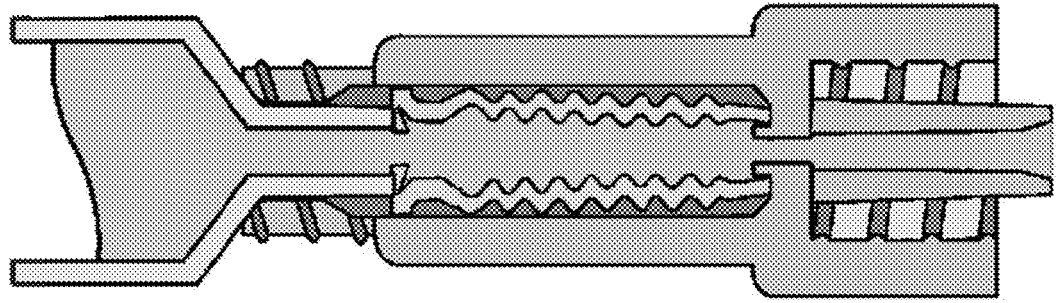
FIGS. 2A-2D are views of luer access devices according to the related art.
Figure 2B:
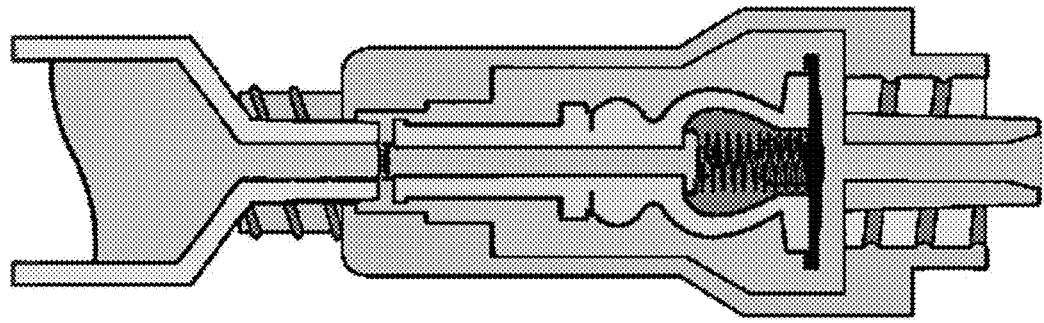
Figure 2C:
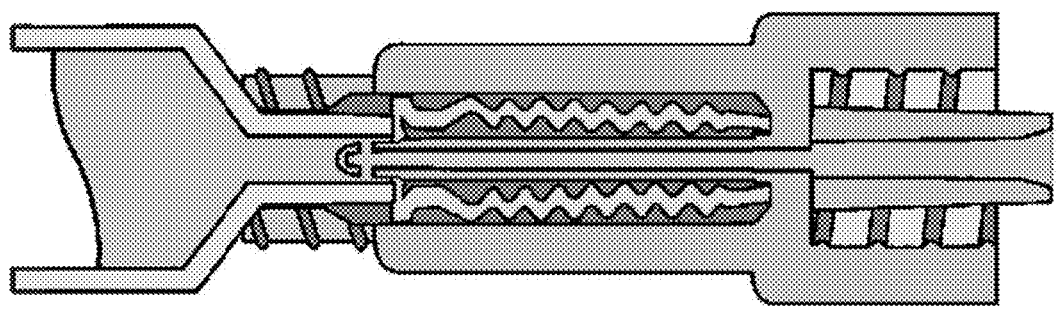
Figure 2D:
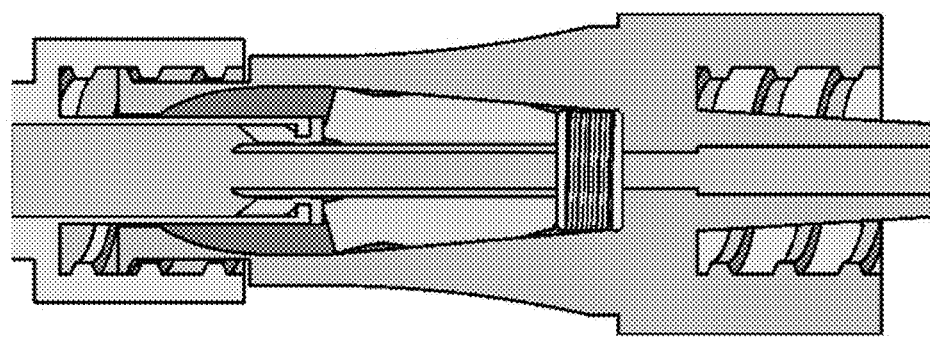

The presently disclosed subject matter will be described more fully hereinafter with reference to the accompanying drawings, in which some, but not all embodiments of the inventions are shown. Like reference numerals refer to like elements throughout. The presently disclosed subject matter may be embodied in many different forms and should not be construed as limited to the embodiments set forth herein; rather these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

In one aspect, the present invention is directed to a luer access device (LAD) having a split septum to provide a sterile connection between luer connectors. In particular, the present invention is directed to an LAD that facilitates a connection with medical articles and reduces the risk of catheter-related bloodstream infections by preventing the ingress of microorganisms through the LAD. The split septum of the LAD in the present invention is opened and specifically deformed to provide fluid communication between the two connectors while preventing external surfaces and surface contaminants from directly contacting the infusion fluid or internal surfaces consisting of the fluid lumen. The prevention of external surfaces that may be exposed to environmental contaminants from contacting the infusion fluid or internal fluid channels ensures that during attachment of the connectors each surface remains sterile, unlike the related art in which external surfaces are disinfected prior to connection of a sterile medical article but are in contact with the fluid upon connection, thus increasing the susceptibility of contamination of the needleless access device and administration fluid.

FIG. 4A illustrates a needleless access system according to an exemplary embodiment of the present invention. As illustrated in FIG. 4A, the access system may include a male connector 400 and a fluid access device 405. The male connector 400 is shown as an adapter, but one skilled in the art will recognize that the novel features of the present invention may be incorporated into any standard attaching article using a male-to-female connection system, including syringes, administration sets, vial adapters, ports, and similar articles. Therefore, the illustration of the male connector 400 as an adapter, and more particularly, as a luer adapter, is not intended to limit the proximal design or coupling mechanism with medical articles common to the art. The novel features of present invention will be described in further detail herein below.

As illustrated in FIGS. 4A-4B, the male connector 400 may include at least one elastomeric member 415 disposed within the distal end of the male connector 400. As shown in the partially sectional view of FIG. 4B, the elastomeric member 415 may temporarily occlude the distal tip of the male connector 400 along the axial direction. In applications where fluid administration requires an attaching medical article to be void of air prior to coupling the male connector 400 to the fluid access device 405, at least one aperture 410 may be disposed at the distal end of the male connector 400 to allow air to escape during the fluid filling thereof. The access device 405 may include a female elastomeric member 420 and an internal cannula 425.

FIG. 5A illustrates an exploded view of the access device assembly according to an exemplary embodiment of the present invention. As illustrated in FIG. 5A, the female elastomeric member 420 may be contained between a top section 500 and bottom section 510. In particular, the female elastomeric member 420 may be partially restrained by the top and bottom sections, allowing the female elastomeric member 420 to return to a starting position after the removal of an attaching male connector. The female elastomeric member 420 has an external surface 515 at the proximal end of the access device and is exposed to the environment, and an internal surface 520 that surrounds an internal cannula 425. The access device of FIG. 5B contains internal surfaces that comprise the fluid flow channel 535 (specifically, all surfaces of the internal cannula 425), and internal surfaces 525 that are not in direct contact with the fluid flow channel 535. The internal cannula 425 contains a region 550 that penetrates the female elastomeric member 420 and at least one aperture 545 accessing the fluid flow channel 535.

FIG. 6A illustrates an exploded view of the male connector assembly according to an exemplary embodiment of the present invention. The assembly of FIG. 6A illustrates the elastomeric member as two separate members 605 and 610 disposed between an insert 600 and jacket 615. In particular, a first elastomeric member 605 may be a valve or split septum which governs fluid flow direction, and a second elastomeric member 610 may have an annular form and operate as a gasket or seal. The elastomeric members 605 and 610 may be combined into a single elastomeric member or may be distinct and assembled in a stacked arrangement as shown. The distal tip of the jacket 615 may include one or more apertures 410 that extend from the distal tip of the jacket 615.

The partially-sectional view of the male connector in FIG. 6B illustrates an exemplary assembly of the components in FIG. 6A. The insert 600 may be joined to the jacket 615 by a locking mechanism 625 which secures the elastomeric members 605 and 610 between the two rigid members. While the male connector of FIG. 6B is depicted as a luer adapter with male and female receiving ends for adapting current medical articles for use with the sterile needleless fluid access system of the present invention, as noted earlier, the insert 600 may be molded in one process with syringes, administration sets, or similar medical articles.

FIG. 6C shows a sectional detailed view of select features of the distal portion of the assembly in FIG. 6B. The sectional view of the elastomeric member is shown for clarity. The figure illustrates that the aperture 410 in the jacket 615 extends to a depth 630 overlapping with an aperture 635 on the insert 600. In an exemplary embodiment of the present invention, the insert 600 is symmetric and the jacket 615 is not symmetric about the sectional plane, thereby containing at least one set of overlapping apertures 630 and 635, and at least one set of non-overlapping apertures 640. In addition, the distal end of the insert 600 may form a seal against the proximal surface of the first elastomeric member 605 with the exception of one or more apertures (or notches). In further detail, the apertures 630 and 635 may not be initially occluded by the first elastomeric member 605, which allows fluid (including air) to flow through the apertures 635 and 630. However, the elastomeric members 605 and/or 610 may occlude one or both apertures 630 and 635 but is either compressible upon a positive fluid pressure from the proximal or distal direction, or contains a one-way valve mechanism to permit fluid flow through the side aperture 410.

Figure 7A:
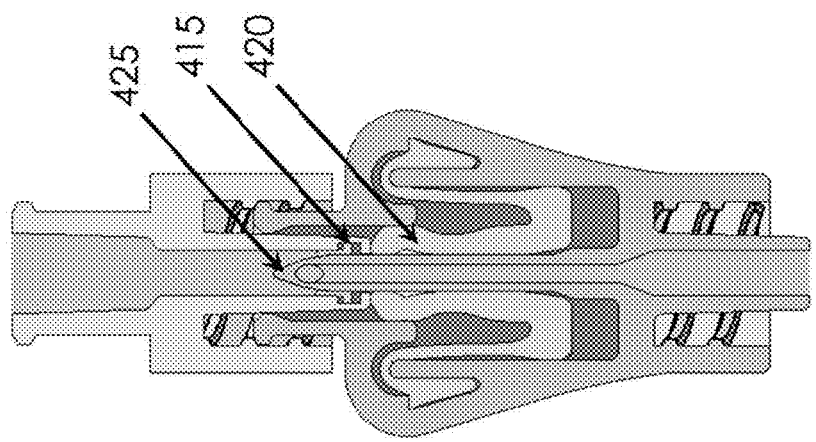
FIGS. 7A-7D are views of engaging a male connector and a access device of the needle-free system according to an exemplary embodiment of the present invention.

Referring to FIGS. 4A-4B, FIGS. 7A-7D illustrate views of engaging the access device 405 and the male connector 400, whereby the internal cannula 425 may be exposed within the proximal female connector 700 of the access device 405, having penetrated the female elastomeric member 420 upon engagement with the male connector 400, and thus penetrate the male elastomeric member 415 for fluid communication between the two fluid fittings. Initially, as seen in FIG. 7A, the access device is sealed by the female elastomeric member 420, and the internal cannula 425 is coupled into an end of the female elastomeric member 420 within a passageway of the proximal female connector 700 of the access device 405. In addition, in FIG. 7A the male connector 400 may be primed but remains sealed in the axial direction.

Figure 7B:
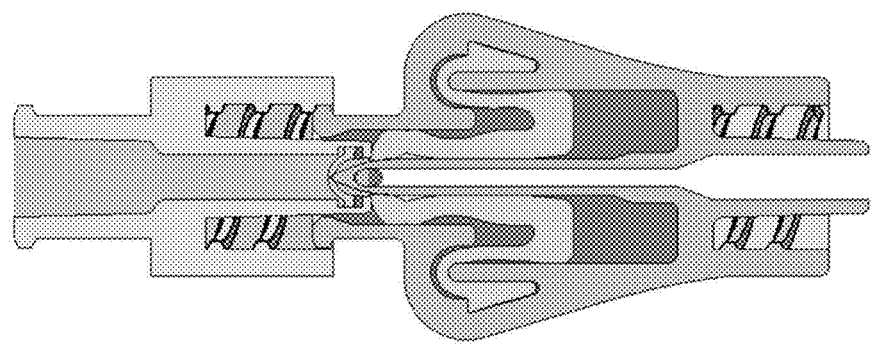

Then, as shown in FIG. 7B, the male connector 400 engages with the female connector 700 of the access device 405, partially displacing the female elastomeric member 420, resulting in the internal cannula 425 to begin to penetrate through and open the female elastomeric member 420. As the male connector 400 engages with the female connector 700 of the access device 405, a region of the female elastomeric member begins to deform under tensile loading.

Figure 7C:
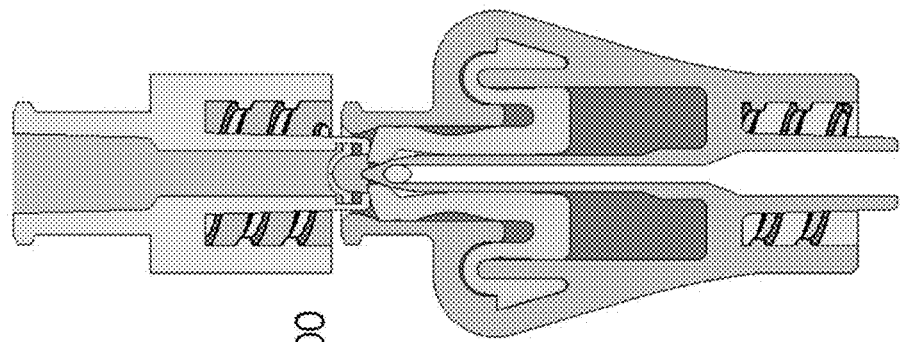

Further, as shown in FIG. 7C, the female elastomeric member 420 has been further displaced in the distal direction along the internal cannula 425 by the attached male connector 400 to expose the proximal tip of the internal cannula 425. While the male connector 400 has engaged with the female connector 700 of the access device 405, the elastomeric member 415 of the male connector 400 has not been fully penetrated by the internal cannula 425 and thus remains sealed in the axial direction.

Figure 7D:
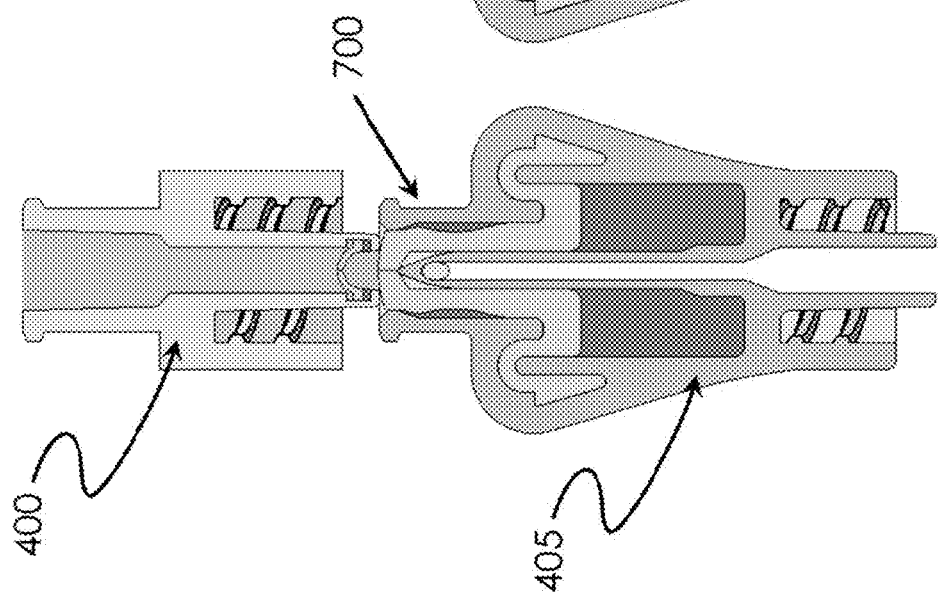

Referring now to FIG. 7D, illustrating the complete engagement of the male and female connectors (i.e., the male connector is seated against the female connector of the access device), the internal cannula 425 penetrates through the male elastomeric member 415 and into the male connector 400 to provide a direct fluid-flow path between the male and female connectors. As also seen in FIG. 7D, the complete engagement of the connectors results in a further elongation of a region of the female elastomeric member 420. Additionally, an interior of the male connector 400 may be threaded to engage with the external wall of the female connector 700 of the access device 405 upon the complete engagement of the connectors as an interlocking mechanism. As will be described in further detail with reference to FIG. 9, once the internal cannula 425 has penetrated into the male connector 400, the elastomeric member 415 seals the internal cannula 425 with the male connector 400, thus providing a sterile connection between the two connectors and the fluid flow path.

FIG. 8 illustrates a detailed view of the female elastomeric member 420 in the partially opened state from FIG. 7B in response to engagement with the distal end of the male connector 400 according to an exemplary embodiment of the present invention. In particular, FIG. 8 shows that the female elastomeric member 420 may be disposed at a proximal end of the fluid access device 405 and may be coupled to an internal surface 525 thereof, having a particular geometric profile (i.e., an engineered geometry). The female elastomeric member 420 may be designed to have a particular geometric shape capable of deforming in a prescribed manner while being opened. Therefore, the particular geometrical shape of the female elastomeric member 420 and the internal surfaces 525 and 820 may prevent the external surface 805 thereof from contacting the internal cannula surface 820. Thus, any potential pathogen remaining on the external surface 805 of the female elastomeric member 420 does not come in contact with (i.e., does not touch) the internal cannula surface 820. Instead, the internal elastomeric surface 830 of the female elastomeric member 420 contacts the internal cannula surface 820 and remains a sterile internal surface.

In other words, as seen in FIG. 8, only an internal surface 830 of the female elastomeric member 420 contacts the internal cannula surface 820 while an external surface 805 of the female elastomeric member 420 is pushed outward due to the deformation of the female elastomeric member 420 and contacts only the internal surface 525 of the fluid access device 405 which is not part of the fluid flow path. Notably, the present invention is not limited to the particular deformation caused by the geometrical features 805, 810, 825, and 830 of the female elastomeric member 420 interfacing with the rigid surfaces 525 and 820 of the fluid access system as shown in FIG. 8. Any geometric deformation may be used as long as an external surface 805 of the elastomeric member 420 does not contact the internal cannula surface 820, thus preventing any potential contamination into the fluid-flow path.

Figure 9:
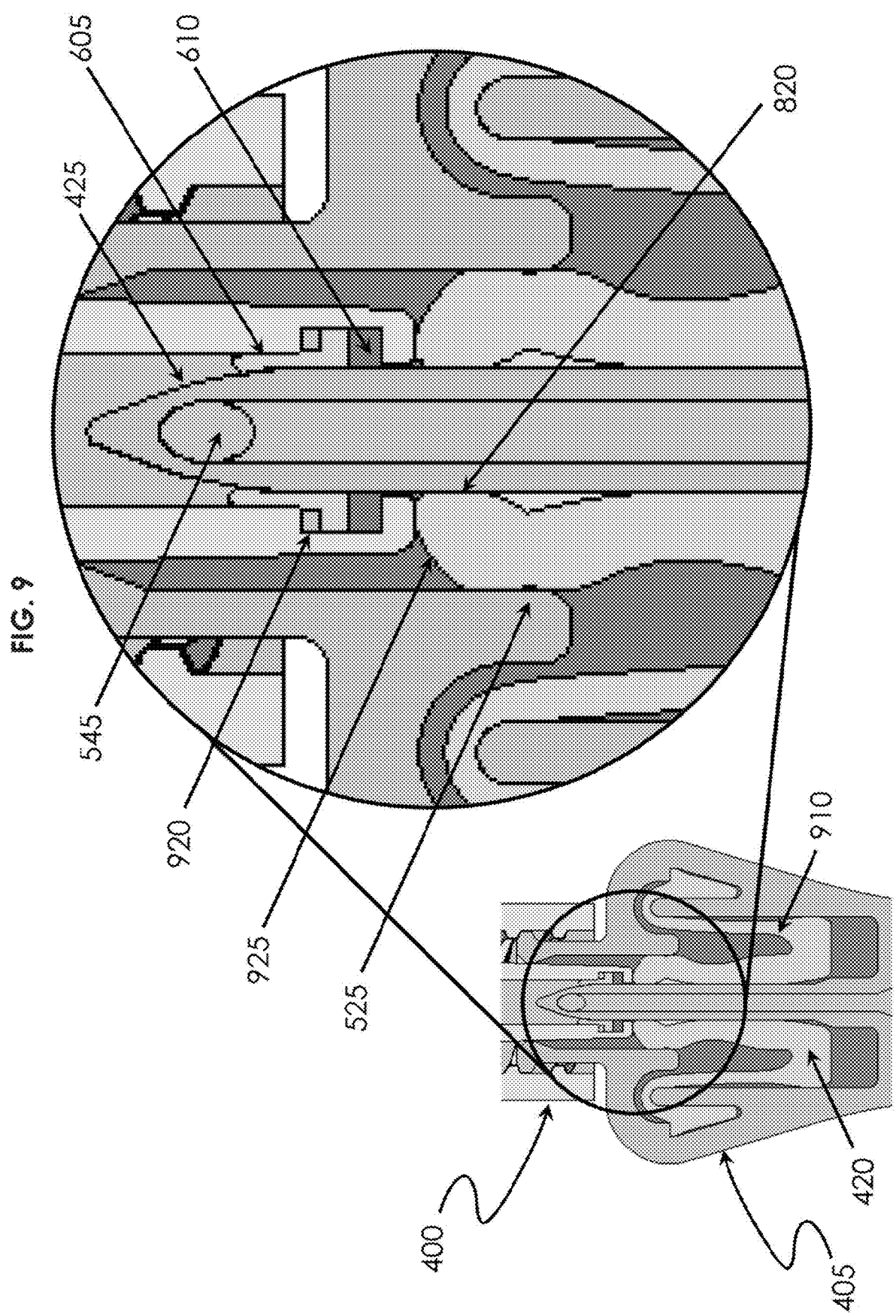
FIG. 9 is a detailed view of the male and female connectors in a fully attached configuration according to an exemplary embodiment of the present invention.

FIG. 9 illustrates a detailed view of the male and female connectors in a fully attached configuration according to an exemplary embodiment of the present invention. Specifically, the male connector 400 may be coupled to an external surface 925 of the female elastomeric member 420 and cause the displacement of the female elastomeric member 420 to move along the axis of the internal cannula 425. As shown in the figure, the female elastomeric member 420 is displaced within the open cavity of the fluid access device 405, and may undergo elastic elongation 910, which provides the stored energy to return the female elastomeric member 420 to an initial position. As seen in the detailed magnification, the female elastomeric member 420 may also undergo compressive forces by certain surfaces of the fluid access device 405 such as 525 and 820, which cause an external surface 925 of the female elastomeric member 420 to deflect away from the internal cannula surface 820. The internal cavity of the fluid access device 405 therefore may have both an open volume to accommodate a displacing female elastomeric member 420 and a formed surface 525 which may deform or compress the female elastomeric member 420 upon engagement with the male connector 400.

Additionally, with regards to FIG. 9, the figure shows a detailed view of the distal male connector 400 including a first elastomeric member 605 and a second elastomeric member 610 secured within the proximal end of the fluid access device 405 according to an exemplary embodiment of the present invention. In particular, the internal cannula 425 has penetrated through the male elastomeric members 610 and 605 to provide fluid communion through at least one aperture 545 of the internal cannula 425. Upon engagement with the internal cannula 425, a first male elastomeric member 605 is displaced and seals an aperture 920 of the distal male connector 400. Further, a second male elastomeric member 610 contains an inner diameter approximately equal to the outer diameter of the internal cannula 425 which forms a seal between the distal male connector 400 and the internal cannula 425. Accordingly, the distal end of the connecting article (e.g., 400) is not sealed against external surfaces 925 of the female elastomeric member 420 as in the related art, but by an elastomeric member 610 within the distal tip of the attaching article. Additionally, conventional needle-free systems such as LADs are often not sealed through the luer taper of the male connector, but through a flush compression of the outer surface of the displaced female elastomeric member against the distal opening of the male luer tip.

FIG. 10A illustrates the female elastomeric member 420 as a split septum according to an exemplary embodiment of the present invention. More specifically, the figure illustrates the split septum having an orientation with respect to the non-radial symmetry of the female elastomeric member 420 (as shown in FIG. 4B). The fluid access device 405 of FIG. 10A is shown in an isometric view, with the proximal female connector 700 illustrated in the magnified section. The female elastomeric member 420 has symmetry about the A1 plane, which is the same perspective of previous sectional illustrations such as FIGS. 7-9. When the female elastomeric member 420 has a slit 1010 through which a member may penetrate (e.g., an internal cannula), the opening profile of the female elastomeric member 420 may be different when viewed from planes A1 (as in FIGS. 7-9) and A2. Therefore, the female elastomeric member 420 of the present invention has a specific orientation of an opening 1010 as part of the engineering design of the female elastomeric member 420.

In further detail to the exemplary embodiment of the present invention shown in FIGS. 10A-10C, the female elastomeric member 420 has a slit 1010 with a long axis in the plane A2 and a short axis in the plane A1. Therefore, upon penetration by a cylindrical member 1020 such as an internal cannula, the slit 1010 may be caused to elongate 1015 along the long axis wider than the diameter of the cylindrical member 1020 (whereas the short axis may maintain a closer coupling to the outer diameter of the cylindrical member as shown in FIG. 10C). In the illustration of FIG. 10B, the proximal end of the fluid access device 405 has been shown as wireframe for clarity, and the illustration of FIG. 10C shows a top-down perspective of the proximal end of the fluid access device 405. The figures show at least one aperture 1025 aligned with the long axis of the slit 1010. Thus, as the female elastomeric member 420 is penetrated by the cylindrical member 1020, the aperture 1025 is aligned with the necking region 1030 of the slit 1010 to prevent the outer surface 1040 of the female elastomeric member 420 from contacting the internal cylindrical body 1020 in the region of one or more apertures 1025. While the slit 1010 is illustrated as a single slit with one set of long and short axes, two or more slits may be used in either orthogonal or other geometric arrangements to align a necking region of the elastomeric member undergoing deformation in a particular orientation to prevent direct contact with a region of the penetrating member. Accordingly, the fluid access system of the claimed invention is capable of providing a fluid flow path of sterile surfaces.

Figure 11:
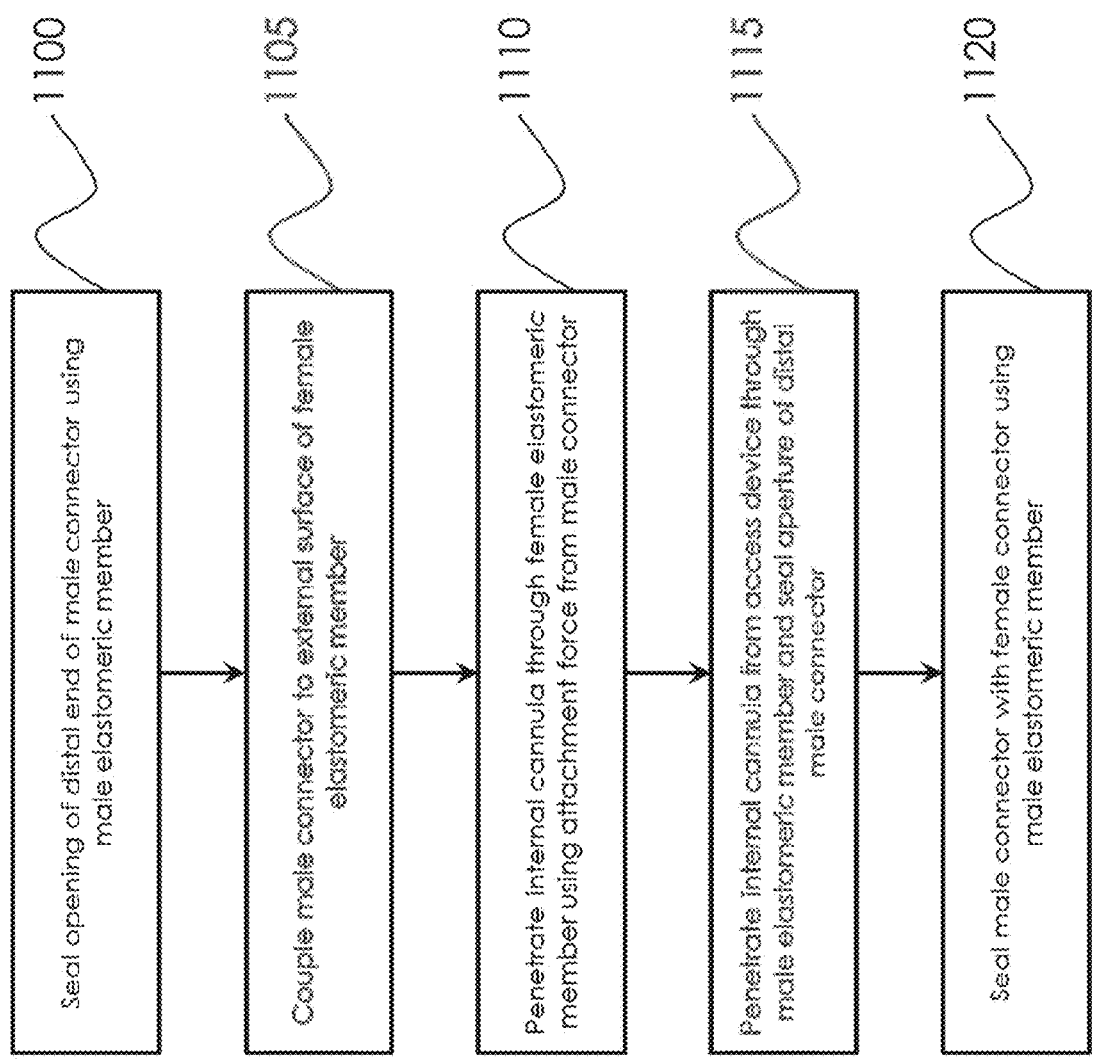
FIG. 11 is a flowchart showing the method of coupling male and female connectors to achieve a sterile connection according to an exemplary embodiment of the present invention.
Figure 12:
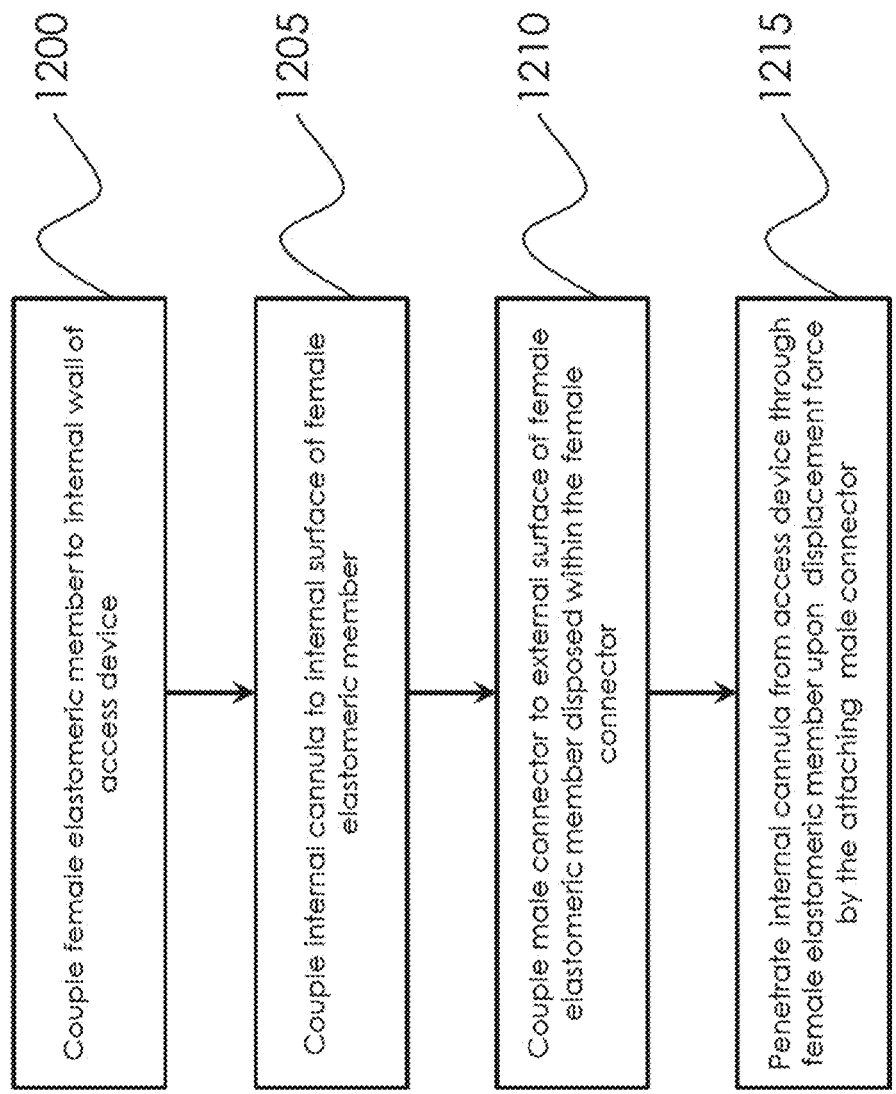
FIG. 12 is another flowchart showing the method of coupling male and female connectors to achieve a sterile connection according to an exemplary embodiment of the present invention.

In another aspect, FIGS. 11 and 12 illustrate an exemplary process for coupling the fluid access system described above according to an exemplary embodiment of the present invention. Referring first to FIG. 11, the process may include sealing an opening of the distal end of a male connector using a male elastomeric member (S1100). Then, the male connector may be coupled to an external surface of a female elastomeric member that is disposed at a proximal end of the fluid access device (S1105). An internal cannula that is disposed in a passageway of the female connector may penetrate through the female elastomeric member to open the female elastomeric member upon engagement with the male connector (S1110). The male elastomeric member may be used to seal an opening of at least one aperture as the internal cannula penetrates through the opened female elastomeric member and the male elastomeric member (S1115). The aperture may include a plurality of apertures that are disposed through a sidewall of the distal end of the male connector. The male elastomeric member may then seal the male connector with the female connector creating a fluid-tight fitting (S1120). The process may then illustratively end when the female connector and the male connector are engaged to provide a sterile fluid communication there between.

Referring now to FIG. 12, the process may include coupling the female elastomeric member to an internal wall of the fluid access device (S1200) and coupling the internal cannula into an end of the female elastomeric member within a passageway of the female connector (S1205). The male connector may then be coupled to an external surface of the female elastomeric member disposed within the female connector (S1210). Further, the female elastomeric member may be opened by the penetration of the internal cannula when coupled with the male connector (S1215). As the female elastomeric member opens, the shape thereof deforms to thus prevent an outer surface from contacting the internal cannula. The process may illustratively end once the female elastomeric member is opened and the internal cannula penetrates into the male connector to couple the male connector and the female connector, providing a sterile fluid communication there between.

As discussed above, the fluid access system of the claimed invention is capable of providing a sterile connection between male and female connectors, creating a sterile fluid-flow path. The particular design of the female elastomeric member in the claimed invention prevents potentially contaminated external surfaces thereof from directly contacting any sterile surfaces of the fluid-flow path. Accordingly, the sterile connection access system of the present invention may be capable of reducing contamination-related infections occurring in the related art of fluid connectors. The methods for coupling a surface of the female septum with the internal surface of the female connector and a male elastomeric member within the male connector may be practical in several types medical connectors that require sterile connecting interfaces, including vascular catheters, enteral devices, lumbar punctures and ventriculoperitoneal shunts, endotracheal tubes, and the like.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A fluid connection system, comprising:
a fluid access device having a female connector with an internal female elastomeric member disposed at a proximal end thereof and coupled to an internal surface of the fluid access device;
a male connector coupled to an external surface of the female elastomeric member;
a male elastomeric member disposed at a distal end of the male connector and that seals a distal opening thereof; and
at least one aperture disposed through a sidewall of the distal end of the male connector;

wherein an internal cannula is exposed out of the female connector to open the female elastomeric member upon an attachment force with the male connector; and wherein the male elastomeric member seals an opening of the at least one aperture following the penetration of the internal cannula.

2. The fluid connection system of claim 1, wherein the male elastomeric member seals an opening of the at least one aperture when the female elastomeric member is opened.

3. The fluid connection system of claim 2, wherein the male elastomeric member is formed of at least two separate elastomeric members in a stacked arrangement.

4. The fluid connection system of claim 2, wherein a distal end of an inner conduit of the male connector forms a seal against a proximal surface of the male elastomeric member.

5. The fluid connection system of claim 1, wherein the female elastomeric member moves along the axial direction of the internal cannula upon engagement with the male connector to expose the internal cannula.

6. The fluid connection system of claim 5, wherein the female elastomeric member is moved in response to an elastic force.

7. The fluid connection system of claim 6, wherein the elastic force is output by the female elastomeric member having undergone tensile elongation.

8. The fluid connection system of claim 7, wherein the elastomeric member undergoes elastic deformation upon engagement with the male connector.

9. The fluid connection system of claim 1, wherein an interior of the male connector is threaded to engage with an external wall of the female connector.

10. The fluid connection system of claim 9, wherein the plurality of apertures are formed as slots extending from the distal end of the male connector.

11. The fluid connection system of claim 1, wherein the distal end of the male connector includes a plurality of apertures.

12. The fluid connection system of claim 1, wherein the internal cannula penetrates into the male connector when the female elastomeric member is opened to provide fluid communication between the male connector and the female connector.

13. The fluid connection system of claim 1, wherein the male and female connectors have tapered surfaces.

14. A method for coupling a fluid connection system, comprising:
   sealing an opening of a distal end of a male connector using a male elastomeric member;
   coupling the male connector to an external surface of a female elastomeric member that is disposed within a female connector at a proximal end of a fluid access device of the fluid connection system;
   penetrating an internal cannula disposed in a passageway of the female connector through the female elastomeric member using an attaching force from the male connector;
   sealing an opening of at least one aperture using the male elastomeric member following the penetration of the internal cannula through the female elastomeric member,
   wherein the at least one aperture is disposed through a sidewall of the distal end of the male connector; and
   sealing the male connector with the female connector of the fluid access device using a male elastomeric member.

15. The method of claim 14, further comprising:
   coupling the female elastomeric member to an internal wall of the fluid access device,
   wherein the female elastomeric member deforms during the opening thereof to prevent an outer surface from contacting the internal cannula.

16. The method of claim 15, further comprising:
   connecting an external fluid line to a distal end of the fluid access device and connecting a fluid line to a proximal end of the male connector.

17. The method of claim 14, wherein the female elastomeric member is moved along the axial direction of the internal cannula in response to an elastic force output by the female elastomeric member.

18. The method of claim 17, wherein the elastomeric member undergoes tensile elastic deformation upon coupling of the female connector and the male connector.

19. The method of claim 14, wherein the male elastomeric member is formed of at least two separate elastomeric members.

20. The method of claim 14, wherein a distal end of an inner conduit of the male connector forms a seal against a proximal surface of the male elastomeric member.

21. The method of claim 14, wherein an interior of the male connector is threaded to engage with an external wall of the female connector.

22. The method of claim 14, wherein the distal end of the male connector includes a plurality of apertures.

23. The method of claim 22, wherein the plurality of apertures are formed as slots extending from the distal end of the male connector.

24. The method of claim 14, wherein the penetration of the internal cannula into the male connector provides fluid communication between the male connector and the female connector.

25. A method for coupling a fluid connection system, comprising:
   coupling a female elastomeric member to an internal wall of a fluid access device of the fluid connection system;
   coupling an internal cannula to an internal surface of the female elastomeric member within a passageway of a female connector;
   coupling a male connector to an external surface of the female elastomeric member; and
   opening the female elastomeric member by penetration of the internal cannula upon coupling with the male connector,
   wherein the female elastomeric member deforms during the opening thereof to prevent an outer surface of the female elastomeric member from contacting the internal cannula, and
   wherein when the female elastomeric member is opened, the internal cannula penetrates into the male connector to couple the male connector and the female connector.

26. The method of claim 25, wherein the female elastomeric member moves along the axial direction of the internal cannula upon disengagement with the male connector in response to an elastic force.

27. The method of claim 26, wherein the elastic force is output by the female elastomeric member having undergone tensile elongation.

28. The method of claim 27, wherein the female elastomeric member undergoes elastic deformation upon coupling of the female and male connectors.

* * * * *